United States Patent [19]
Wessling et al.

[11] Patent Number: 5,089,259
[45] Date of Patent: Feb. 18, 1992

[54] STABLE CONCENTRATES AND EMULSIONS OF WATER-INSOLUBLE ORGANIC PESTICIDES

[75] Inventors: Ritchie A. Wessling, Berkeley, Calif.; Dale M. Pickelman, Auburn, Mich.; Dennis G. Wujek, Midland, Mich.

[73] Assignee: DowElanco, Indianapolis, Ind.

[21] Appl. No.: 400,418

[22] Filed: Aug. 30, 1989

Related U.S. Application Data

[63] Continuation-in-part of Ser. No. 286,569, Dec. 19, 1988, abandoned.

[51] Int. Cl.$^5$ .................. A61K 31/74; A61K 31/78; A01N 27/00; A01N 29/00
[52] U.S. Cl. ............................ 424/497; 424/405; 424/407; 424/419; 523/122
[58] Field of Search .................. 424/78, 81, 407, 405, 424/419; 523/122

[56] References Cited

U.S. PATENT DOCUMENTS

| | | | |
|---|---|---|---|
| 3,400,093 | 9/1968 | Feinberg | 260/29.6 |
| 4,036,788 | 7/1977 | Steckler | 514/295 |
| 4,199,363 | 4/1980 | Chen | 430/512 |
| 4,203,716 | 5/1980 | Chen | 430/207 |
| 4,303,642 | 12/1981 | Kangas | 424/295 |
| 4,337,185 | 6/1982 | Wessling | 524/458 |
| 4,427,819 | 1/1984 | Wessling et al. | 524/458 |

OTHER PUBLICATIONS

Rogiers et al., "Novel Trends in Dispersants", *Sixth International Congress of Pesticidal Chemistry*, Ottawa, Canada, Aug. 10–15, 1986.

*Primary Examiner*—Lester L. Lee

[57] ABSTRACT

Stable, aqueous emulsion formulations of water-insoluble organic pesticides are formed from a mixture of (1) a water-insoluble organic pesticide, (2) a water based structured particle latex containing nonionic particles to which is bound a layer containing stabilizing pH independent ionic groups chemically bound at or near the surface of the polymer particles, and optionally a cosolvent and/or cosurfactant for the pesticide. The resulting product is much more stable to coalescence than emulsions made with conventional surfactants.

15 Claims, No Drawings

STABLE CONCENTRATES AND EMULSIONS OF WATER-INSOLUBLE ORGANIC PESTICIDES

CROSS-REFERENCE TO RELATED APPLICATION

This application is a continuation-in part of Ser. No. 286,569 filed Dec. 19, 1988, and now abandoned.

BACKGROUND OF THE INVENTION

As shown in U.S. Pat. No. 3,400,093 issued Sept. 3, 1968 to Irving Feinberg, known methods for incorporating pesticides into water-based systems have been unsatisfactory in that the pesticides tend to settle out and do not remain uniformly dispersed. Feinberg proposed to solve that problem by emulsion polymerization of monomers in the presence of the pesticide. However, certain pesticides, such as chlorpyrifos and chlorpyrifos-methyl, tend to hydrolyze if heated to polymerization temperatures for extended periods of time and, in addition, the presence of a pesticide in a monomer will influence the polymerization to some degree, e.g., the rate of polymerization, the conversion and/or the molecular weight of the polymer.

Kangas, in U.S. Pat. No. 4,303,642 issued Dec. 1, 1981, proposed to solve the above problems by adding the pesticide to a finished latex wherein the polymeric particles were in a size range of from 0.03 to 20 microns, and increases in pesticide efficiency were, indeed demonstrated, although optimum stability and transfer through soil were not obtained.

Rogiers and Bognolo, in a paper presented at the Sixth International Congress of Pesticide Chemistry, Ottawa, Canada, Aug. 10–15, 1986, reported on the stabilization of an Ethirincol suspension concentrate with a graft stabilizer of a polymethylmethacrylate-polymethacrylic acid grafted with polyethylene oxide.

T.J. Chen, in U.S. Pat. Nos. 4,199,363 and 4,203,716, discloses a process for uniformly dispersing hydrophobic materials through hydrophilic colloid layers, such as photographically useful layers containing gelatin.

Soil pesticides are usually incorporated into the soil mechanically or are spread on the soil surface to be leached into the soil by rainfall. In either case, the pesticide may not be able to function properly because it becomes immobilized at the point of application. This will certainly be the case for large hydrophobic molecules and the problem is compounded further if the carrier is itself a large hydrophobic particle.

SUMMARY OF THE INVENTION

In accordance with this invention, stable aqueous emulsion formulations of water insoluble organic pesticides are formed by swelling the particles of a structured particle latex with the pesticide, said latex comprising polymer particles (carrier) with a nonionic core that is compatible with the pesticide and a stabilizing ionic surface layer containing stabilizing pH independent ionic groups chemically bound at or near the surface of the polymer particles.

The latex can optionally contain (1) a compatibilizing or coupling solvent, (2) a plasticizer or swelling agent for the particle that is also a solvent for the pesticide and (3) a cosurfactant.

Preferably the surface layer is formed by grafting a reactive polymeric surfactant (RPS) to the nonionic polymer core thus rendering the ionic stabilizing groups non-desorbable. Grafting may be carried out during the formation of the core particle itself or by reaction of the RPS with a preformed latex formed by emulsion polymerization or emulsification of an existing polymer.

It has been found that the said structured particle latex spontaneously absorbs organic pesticides with low water solubility upon simple mixing. The resulting product is more stable to coalescence than emulsions made with conventional or polymeric surfactants.

Because the ionic surface layer is bound to the particle, the concentration of ionic groups can be much higher than is possible with a conventional latex, and the latex retains colloidal stability even under extreme conditions such as high water dilution in the soil.

In forming the compositions of this invention, the process allows each component to be independently optimized to provide the most effective desired emulsion. The composition of the surface layer is selected to provide colloidal stability. The composition of the core is selected to provide compatibility with the pesticide.

Ideally, the carrier employed to transport the pesticide should be a small hydrophilic colloidal particle with a high negative charge to promote rapid movement in the soil. In order to be effective, however, the particle must be stable against flocculation by polyvalent cations in the soil, and the ionic groups must be bound to the particle to avoid redistribution of the stabilizing groups, i.e., surfactant, to the surface of the soil particles. Because carboxylated latexes are not stable against flocculation by polyvalent cations they are not suitable for this use.

In conventional formulations the surfactants are absorbed on the particle surface and are in equilibrium with the aqueous phase and the surface of soil particles. Since the surface area is so large, the soil tends to act as an infinite sink of low surfactant concentration and much of the surfactant initially on the pesticide particle transfers to the soil, whereupon the pesticide particle either deposits on the soil or flocculates, thereby losing the ability to migrate through the soil. In the present invention the problems of a lack of the ability of the particle to migrate through the soil is avoided.

DETAILED DESCRIPTION OF THE INVENTION

The preferred structured particle latexes that can be used in the present invention include those aqueous based latexes described in U.S. Pat. Nos. 4,337,185 and 4,427,819, which are incorporated herein by reference thereto. Such latexes advantageously have stabilizing ionic groups chemically bound at or near the surface of the polymer particles which are dispersed in aqueous media.

The pesticidal formulations can be first prepared as a water-dilutable emulsion concentrate by blending the active pesticidal ingredient, in the liquid state, with the water based structured particle latex, with agitation, for a sufficient time for the active ingredient to diffuse into the particles. If the active ingredient is not a liquid per se, it can be melted or dissolved in a water-immiscible solvent. If it is too insoluble to migrate through the aqueous phase of the latex into the polymer particles, it may be necessary to add a partially water compatible coupling solvent or a nonionic surfactant to facilitate mixing. The coupling solvent can be optionally stripped from the mixture after the swelling. The coupling solvent preferably boils below the boiling point of water.

Representative water miscible coupling solvents, include, for example, acetone, methyl ethyl ketone, tetrahydrofuran and $C_1$–$C_4$ alcohols to facilitate migration of the pesticide with low water solubility through the aqueous phase. The coupling solvent can be optionally stripped from the mixture after the pesticide is incorporated. The swollen anionic particles are, in a colloidal sense, very stable, maintaining their identity in the soil and functioning as a reservoir of the pesticide, which when applied can move through the soil. The swollen cationic particles are stable when sprayed aerially providing enhanced adhesion to foliage and, if desired, they provide immobilization of the pesticide on the soil surface for special pesticidal uses.

The formulation may contain cosolvents which act as swelling agents or plasticizers to improve compatibility of polymer and pesticide. In addition to reducing the Tg of the polymer, the plasticizers can also depress the melting point of crystalline pesticides and aid in release after application.

Suitable plasticizers include, for example, methyl esters of fatty acids such as caproic, lauric, myristic, oleic and tallowic: glycerides such as the oils of cottonseed, soybean, castor bean, corn; and triacetin, Citroflex ® A4 and alkyl aromatics. Preferred plasticizers are Citroflex ® A4, and the methyl esters of caproic, lauric and oleic acid.

It may be advantageous to also employ a cosurfactant, such as nonionic ethylene oxide adducts of alkyl phenols to facilitate transfer of the pesticide or a pesticide solution through the aqueous phase to the hydrophobic core of the particle. Such surfactants are not necessary for stabilizing the emulsion once formed. Useful pesticide solutions are solutions of pesticides and cosolvents that retain fluid character, i.e., noncrystalline state within the carrying particle for optimum low temperature stability and formulation reconstitution after freeze-thaw cycling.

Representative water insoluble organic pesticides useful in the practice of the present invention include one or more pesticides from the classes of acylurea insecticides, organophosphorous insecticides, pyrethroid insecticides, aryloxyaryl herbicides and sulfonamide herbicides. Examples of such pesticides include the acylurea insecticides described in U.S. Pat. Nos. 4,148,902; 4,173,637 and Reissue 30,563, which are incorporated herein by reference, and especially 1-[3,5-dichloro-4-((5-trifluoromethyl)-3-chloro-2-pyridyl-oxy)phenyl]-3-(2,6-difluorobenzoyl) urea (common name Chlorfluazuron):

the organophosphorous insecticides described in U.S. Pat. Nos. 3,244,586; 4,429,125; 4,654,329 and 4,729,987 which are incorporated herein by reference, especially chlorpyrifos and chlorpyrifos methyl:

the pyrethroid insecticides such as cypermethrin, permethrin and fenvalerate:

the aryloxyaryl herbicides described in U.S. Pat. Nos. 4,550,192; 4,551,170 and 4,750,931 which are incorporated herein by reference, especially 2-(4-((5-trifluoromethyl)-2-pyridinyl)oxy)phenoxy)propanoic acid: 2-(4-((3-chloro-5-trifluoromethyl)-2-pyridinyl)oxy)phenoxy)propanoic acid, methyl ester: 2-(4-((3-chloro-5-trifluoromethyl)-2-pyridinyl)oxy)phenoxy)propanoic acid, ethyl ester; and 2-(4-((3-fluoro-5-trifluoromethyl)-2-pyridinyl)oxy)phenoxy)propanoic acid, methyl ester: and the sulfonamide herbicides described in U.S. Pat. Nos 4,731,446; 4,740,233; 4,741,764 and 4,755,212 which are incorporated herein by reference, especially N-(2,6-dichlorophenyl) -5,7-dimethoxy-1,2,4-triazolo(1,5a)pyrimidine -2-sulfonamide: N-(2,6-dichloro-3-methylphenyl) -5,7-dimethoxy-1,2,4-triazolo(1,5a) -pyrimidine-2-sulfonamide: N-(2,6-dichlorophenyl) -5-methyl-7-methylthio-1,2,4-triazolo(1,5a)pyrimidine-2-sulfonamide: N-(2-trifluoromethylphenyl)-5-methyl-7-methylthio -1,2,4-triazolo-(1,5a)pyrimidine-2-sulfonamide: N-(2,6-dichloro-3-methylphenyl) -7-methoxy-5-methyl-1,2,4-triazolo(1,5a) -pyrimidine-2-sulfonamide: and N-(2,6-dichloro -3-methylphenyl)-7-ethoxy-5-methyl-1,2,4-triazolo(1,5a)pyrimidine-2-sulfonamide.

Generally the amount of the water insoluble organic pesticides which can be present in association with the particles of the structured particle latex is in the range of from about 1:50 to about 10:1 in terms of a weight ratio of the pesticide to the particles of the structured particle latex.

The core polymer composition is selected to compatibilize the particle with the active ingredient. The polymer must be substantially water insoluble and present in sufficient amount to form a structured particle in water.

Preferably the core polymer of the structured particle composition has a glass transition temperature (Tg) below the use temperature preferably less than 30° C. (The Tg is easily determined using conventional differential thermal analysis). Compatibility with the active ingredient can be tailored by copolymerizing the appropriate nonionic hydrophobic monomers. Selection can be made on the basis of a typical formulation scheme employing, e.g., known solubility parameters.

Typical monomers useful in preparing copolymers used in forming the core of the structured particles of this invention include, for example, styrenics, acrylates, methacrylates, isoprene, butadiene, acrylonitrile, ethylene, vinyl acetate, vinyl chloride and vinylidene chloride. By copolymerization, polymers having desired compatibility with the pesticides can be prepared using solubility parameters to select the desired composition.

The preferred formulations are anionic and the reactive polymeric surfactant (RPS) in these cases is selected to optimize stability and migratory ability of the particle in the soil. Such surfactants are obtained by using a combination of pH independent anionic monomers and nonionic monomers. Combinations of sulfonate monomers and nonionic hydrophobic and hydrophilic units form the RPS backbone. Preferably, the backbone of the RPS is formed by the copolymerization of ethylenically unsaturated monomers.

The nonionic, hydrophobic units suitably are derived from any copolymerizable ethylenically unsaturated monomer which, when in the form of an amorphous homopolymer, would have a solubility in water of less than 0.1 percent. Specifically, styrene and/or methyl methacrylate function as the nonionic hydrophobic units. However, it should be noted that a backbone containing nonpolar sequences like styrene will require proportionately more ionic or hydrophilic units to achieve the same level of activity.

In some cases, it is advantageous to employ small amounts (e.g., usually less than about 15 weight percent and preferably from 0 to about 5 weight percent based upon the weight of the instant reactive polymeric surfactants) of very hydrophilic but not ionic comonomers for control of the surface activity and water solubility of the interpolymeric polyelectrolyte without having to use more of the ionic comonomers. Acrylamide, methacrylamide, hydroxyethyl acrylate and hydroxypropyl acrylate are particularly useful for this purpose.

Low concentrations of monomers with weak acid or weak base groups and salts thereof may also be used provided that the pH independence of the RPS is not substantially altered, e.g., a minor amount of a vinyl monomer such as acrylic acid or aminoethyl methacrylate (or the hydrochloride salt thereof) could be included to promote adhesion, serve as reactive sites, etc.

The following examples illustrate the present invention and the manner by which it can be practiced, but as such, are not to be construed as limitations upon the overall scope of the same. In the following examples, all parts are by weight unless otherwise specified and the latexes 1 through 4 of Examples I through IV are comparative latexes which are not useful in the present invention.

EXAMPLE I

Latex #1 Rubber Latex Stabilized With Surfactant

The rubber particles are crosslinked styrene/butadiene copolymer (7 percent styrene, 93 percent butadiene) having average diameters of 1100 Å as measured by Brice Phoenix Light Scattering Unit. The particles are stabilized in the latex with 3 percent sodium dodecylbenzene sulfonate based on polymer The concentration measures 32.7 percent solids in water. This latex fails the (a) acetone dilution test,
(b) the freeze-thaw test and
(c) the pesticide formulation freeze-thaw stability test.

(a) Acetone Dilution Test 1 part by weight of Latex #1 diluted with water to a 20 percent solids content was added to 9 parts acetone. No observable coagulation is considered to pass the test.

(b) Freeze-Thaw Test

20 Grams sample at −10° C. to −15° C. for at least 4 hours and then at 35° C. for one hour. No observable flocculation or viscosity increase is considered to pass the test.

| (c) Pesticide Formulation | |
|---|---|
| | (Parts by weight) |
| Chlorpyrifos | 2.0 |
| Methyl Laurate | 1.0 |
| Ethoxylated Nonyl Phenol Surfactant | 1.0 |
| Latex #1 | 1.0 |
| Water | Balance |
| | 10 |

EXAMPLE II

Latex #2 Rubber Latex Stabilized With Post-Added (RPS⊖)

A base polymeric surfactant is prepared by adding 1000 parts of isopropanol and 650 parts of deionized water to a stirred reactor provided with a nitrogen atmosphere and maintained at 50° C. while continuously adding reactants to the reactor from five separate sources with proportionate feeds over 120 minutes. Feed compositions are as follows:

| PARTS | | COMPONENTS |
|---|---|---|
| 1000 | Feed #1 | Deionized water |
| 384 | | 2-Sulfoethyl methacrylate |
| 62.2 | | Dimethylaminoethyl methacrylate |
| 554 | Feed #2 | Methyl methacrylate |
| 6.18 | Feed #3 | 2-Mercaptoethanol |
| 114 | | Deionized water |
| 2.00 | Feed #4 | tertiary-butyl hydroperoxide |
| 118 | | Deionized water |
| 1.50 | Feed #5 | Sodium formaldehyde hydrosulfite |
| 118.5 | | Deionized water |

2500 parts of deionized water are added to the reaction mixture followed by volatilization therefrom of 1700 parts of said water/isopropanol mixture. The resulting water soluble polymeric surfactant is converted t a reactive polymeric surfactant with pendant methacrylate vinyl sites by mixing with 56.3 parts glycidyl methacrylate while heating for 2 hours at 50° C. (RPS⊖). The reactive polymeric surfactant, RPS⊖, has a solid content of 22.1 percent (21.8 percent solids in water, by material balance), a total anionic charge of 1.87 milliequivalents per gram of solids and a number average molecular weight of less than 40,000.

The (RPS⊖) having pendant methacrylate groups is post added to the rubber latex described as Latex #1. 63.5 Parts of (RPS⊖) at 22.1 percent solids, in water, is added to 220.2 parts of Latex #1 and stirred overnight. The concentration of solids measures 30.3 percent. This latex fails the acetone dilution test, the freeze-thaw test, and the pesticide formulation room temperature stability test.

EXAMPLE III

Latex #3 Rubber Latex Encapsulated With Styrene/Normal-Butyl Methacrylate 1.00 Part 2,2′-azobis (2-methylpropanenitrile) is mixed with 764.5 parts of Latex #1 and heated to 70° C. while stirring under a nitrogen atmosphere. 50 Parts of a 50/50 solution of styrene and normal(n)-butyl methacrylate are added continuously using the following schedule: 0 to 20 percent of monomers added over 2½ hours at 70° C. and the remaining 80 percent of monomers added over 1½ hours at 80° C. The reaction conditions are maintained for an additional 2 hours. The latex measures 36.2 percent solids in water, fails the acetone and freeze-thaw stability and pesticide formulation stability tests.

EXAMPLE IV

Latex #4 Rubber Latex Encapsulated With Styrene n-Butyl Methacrylate And Post-Added (RPS⊖)

63.5 Parts of (RPS⊖) at 22.1 percent solids is added to 237.6 parts of Latex #3 and stirred overnight. The mixture measures 33.2 percent solids in water. The latex fails the acetone dilution test, the freeze-thaw test, and the pesticide formulation room temperature stability test.

EXAMPLE V

Latex #5 Rubber Latex Grafted With Styrene n-Butyl Methacrylate And (RPS⊖) To Form Structured Particles 1.00 Part of 2,2'-azobis (2-methylpropane-nitrile) is mixed with 764.5 parts of Latex #1 and heated to 70° C. while stirring under a nitrogen atmosphere. 50 Parts of a 50/50 solution of styrene and n-butyl methacrylate is added continuously with 227.3 parts of (RPS⊖) solution at 22.1 percent solids in water using the following schedule: 0 to 20 percent of monomers added over 2½ hours at 70° C. and the remaining 80 percent monomers added with 0 to 100 percent of (RPS⊖) solution over 1½ hours at 80° C. The reaction conditions are maintained for an additional 2 hours. The latex measures 32.8 percent solids, passes the acetone dilution, freeze-thaw stability and pesticide formulation freeze-thaw stability tests.

EXAMPLE VI

| Ingredient | Weight Ratio |
| --- | --- |
| Chlorpyrifos | 3.0 |
| Methyl Laurate | 1.0 |
| Ethoxylated Nonyl Phenol Surfactant (Igepal 620 ®) | 1.0 |
| Latex comprising 71.4 percent of a rubber core of 7 percent styrene and 93 percent butadiene with a surface graft (14.3 percent) of a 50-50 copolymer of styrene and η-butyl methacrylate and 14.3 percent of an anionic reactive polymeric surfactant comprising 73.7 percent methyl methacrylate, 21.1 percent 2-sulfoethyl methacrylate, 5.27 percent inner salt and glycidyl methacrylate | 1.0 (solids) |
| Deionized Water | 5.4 |

This formulation contained 26.3 weight percent chlorpyrifos.

EXAMPLE VII

The same ingredients as above were employed to give a formulation containing 17.5 weight percent chlorpyrifos wherein the weight ratios were:

| | |
| --- | --- |
| Chlorpyrifos | 2.0 |
| Methyl Laurate | 2.0 |
| Igepal 620 ® | 1.0 |
| Latex #5 | 1.0 |
| Deionized Water | 5.4 |

EXAMPLE VIII

As above in EXAMPLE VII except that the mixture contains 88.8 weight percent chlorpyrifos with the weight ratios:

| | |
| --- | --- |
| Chlorpyrifos | 1.0 |
| Methyl Laurate | 3.0 |
| Igepal 620 ® | 1.0 |
| Latex | 1.0 |
| Deionized Water | 5.4 |

The above formulations when diluted with water to about 1 percent formulation showed good bloom, freeze-thaw and non-settling characteristics.

EXAMPLE IX

Soil Penetration Evaluation

A formulation comprising in parts by weight

| | |
| --- | --- |
| Chlorpyrifos | 2.0 |
| Methyl Laurate | 2.0 |
| Igepal 620 ® | 1.0 |
| Latex of Example V | 1.0 |
| Deionized Water | 5.4 | was prepared. An amount containing 500 mg of formulated chlorpyrifos in 3.0 ml volume was diluted to 50 ml total volume with deionized water and introduced onto a 2 inch diameter 18 inch high column containing about 1150 grams dry soil (Midland, Michigan). The column was then eluted with about 650 ml deionized water and 450 ml of eluent was collected. The column was then frozen and cut into 4 equal quarters and analyzed for chlorpyrifos concentration by extracting with cyclohexane. Two separate columns were tested with the following results:

| | Quarter | Mg Chlorpyrifos | Percent Distribution | Percent Recovery |
| --- | --- | --- | --- | --- |
| Column A | 1 (top) | 277.5 | 61.7 | |
| | 2 | 130.9 | 29.1 | 99.0 |
| | 3 | 33.4 | 7.4 | |
| | 4 | 7.8 | 1.7 | |
| Column B | 1 (top) | 282.5 | 61.7 | |
| | 2 | 132.5 | 28.9 | 92.1 |
| | 3 | 34.5 | 7.5 | |
| | 4 | 8.6 | 1.9 | |

The concentration of chlorpyrifos at the lower depths indicates that 100 percent control of western spotted cucumber beetle larva would be achieved at depths greater than 13 inches.

In contrast to the above soil penetration data, similar tests with previously known latex-pesticide formulations such as, for example, the compositions of U.S. Pat. No. 4,303,642, show that greater than 90% of the pesticide is retained in the top quarter of the soil column. This finding confirms the evaluations of said U.S. patent which indicated that using the formulation of said U.S. patent, 100 percent control of western spotted cucumber beetle larva was only achieved to a depth of 4 to 5 inches.

Because of the greater soil penetrability of the compositions of this invention, less than 65 percent of the pesticide is retained in the top quarter and greater than 35 percent of the pesticide migrates to lower levels as indicated above and 100 percent control of western spotted cucumber beetle larva would be obtained at levels down to 18 inches.

EXAMPLE X

Biological Activity

The organic pesticides employed in the stable aqueous emulsion formulation of the water insoluble organic pesticide/latex mixtures of the present invention have all been found to be as active biologically as when the pesticide is used in conventional formulations. Foliar and soil activity data are shown in Tables I and II respectively for the formulation of Example VII.

TABLE 1

Four-day residual toxicity of chlorpyrifos in formulation to beet armyworm on cotton leaves. Percent mortality was evaluated 72 hours after infestation

| Chlorpyrifos concentration (ppm) | Percent Mortality |
| --- | --- |
| 400 | 100 |
| 100 | 100 |
| 25 | 2 |
| 6.3 | 2 |
| 1.6 | 4 |
| control | 0 |

TABLE 11

Thirty-day residual toxicity of chlorpyrifos in formulation to western spotted cucumber beetle in California sandy loam soil. Percent mortality was evaluated 72 hours after infestation.

| Chlorpyrifos concentration (ppm) | Percent Mortality |
| --- | --- |
| 5.00 | 100 |
| 2.50 | 95 |
| 1.25 | 100 |
| 0.63 | 75 |
| 0.31 | 50 |
| 0.15 | 46 |
| control | 7 |

We claim:

1. A stable aqueous emulsion formulation of a water-insoluble organic pesticide said emulsion comprising
    (1) from about 1 part to about 10 parts by weight of a water-insoluble organic pesticide and from about 50 parts to about 1 part by weight of
    (2) a water based structured particle latex compatible with the pesticide and which is composed of nonionic polymer particle cores to which is bound a stabilizing layer containing stabilizing pH independent ionic groups chemically bound at or near the surface of the polymer particle cores and
    (3) water.

2. An emulsion formulation as defined in claim 1 wherein the stabilizing layer is formed by binding a reactive polymeric surfactant to the surface of a nonionic polymer particle core.

3. An emulsion formulation as defined in claim 2 Wherein the nonionic polymer particle cores are from the group consisting of butadiene and acrylate based nonionic polymers.

4. An emulsion formulation as defined in claim 1 wherein the structured particle latex comprises a reactive polymeric surfactant comprised of a copolymer of a pH independent anionic monomer and a nonionic monomer.

5. An emulsion formulation as defined in claim 4 wherein the nonionic monomer is methyl methacrylate.

6. An emulsion formulation as defined in claim 4 wherein the anionic monomer is 2-sulfoethyl methacrylate.

7. An emulsion formulation as defined in claim 7 wherein a cosolvent is also present.

8. An emulsion formulation as defined in claim 7 wherein the cosolvent for the pesticide is methyl laurate.

9. An emulsion formulation as defined in claim 1 wherein a cosurfactant is also present.

10. An emulsion formulation of as defined in claim 7 wherein the pesticide is chlorpyrifos.

11. An emulsion formulation as defined in claim 1 wherein the pesticide is chlorpyrifos.

12. A method for the control of the growth of agricultural pests in foliar or soil environments which comprises contacting said pest or their foliar or soil environments with a pesticidally effective amount of a stable aqueous emulsion formulation as defined in claim 1.

13. A method as defined in claim 12 whereby the pesticide is chlorpyrifos.

14. The method as defined in claim 13 wherein the pest is corn rootworm.

15. The method as defined in claim 13 wherein the pest is beet armyworm.

* * * * *